(12) United States Patent
Champie

(10) Patent No.: US 10,842,738 B1
(45) Date of Patent: *Nov. 24, 2020

(54) NASAL SPRAY USING C60 AND CURCUMIN

(71) Applicant: Max C. Champie, Buena Vista, CO (US)

(72) Inventor: Max C. Champie, Buena Vista, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 16/749,916

(22) Filed: Jan. 22, 2020

Related U.S. Application Data

(63) Continuation-in-part of application No. 16/565,104, filed on Sep. 9, 2019.

(51) Int. Cl.
| | | |
|---|---|---|
| *A61K 31/19* | (2006.01) | |
| *A61K 31/232* | (2006.01) | |
| *A61K 9/00* | (2006.01) | |
| *A61K 33/44* | (2006.01) | |
| *A61K 36/9066* | (2006.01) | |
| *A61K 36/71* | (2006.01) | |
| *A61K 36/28* | (2006.01) | |
| *A61K 36/63* | (2006.01) | |
| *A61K 36/889* | (2006.01) | |
| *A61K 36/54* | (2006.01) | |

(52) U.S. Cl.
CPC .......... *A61K 9/0043* (2013.01); *A61K 9/0073* (2013.01); *A61K 31/19* (2013.01); *A61K 31/232* (2013.01); *A61K 33/44* (2013.01); *A61K 36/28* (2013.01); *A61K 36/54* (2013.01); *A61K 36/63* (2013.01); *A61K 36/71* (2013.01); *A61K 36/889* (2013.01); *A61K 36/9066* (2013.01)

(58) Field of Classification Search
None
See application file for complete search history.

(56) References Cited

U.S. PATENT DOCUMENTS

2010/0179103 A1* 7/2010 Desai .................. B82Y 5/00
  514/58
2018/0008629 A1* 1/2018 Dixit .................. A61K 45/06

FOREIGN PATENT DOCUMENTS

WO   WO-2015086239 A1 *  6/2015  ........... A61K 36/315

OTHER PUBLICATIONS

Alam et al., "Development and evaluation of thymoquinone-encapsulated chitosan nanoparticles for nose-to-brain targeting: a pharmacoscintigraphic study," International Journal of Nanomedicine 2012:7 5705-5718.*

* cited by examiner

*Primary Examiner* — Jared Barsky
(74) *Attorney, Agent, or Firm* — Fish IP Law, LLP

(57) ABSTRACT

A nutraceutical composition comprising fullerene (e.g., C60), curcumin, and a medium chain triglyceride. Preferably, blackseed oil is used to provide medium chain triglyceride. The nutraceutical composition can be packaged in a mist-producing device and used as a nasal spray or an inhaler. Preferably, the nasal spray is substantially free of particles having a size greater than 0.2 μm. The nutraceutical composition can be used to treat respiratory conditions (e.g., asthma, nasal polyps, etc.) or brain disorders through nasal spray, inhaling, or oral administration.

13 Claims, 1 Drawing Sheet

NASAL SPRAY USING C60 AND CURCUMIN

CROSS-REFERENCE TO RELATED APPLICATIONS

This application claims priority to, and is a continuation in part (CIP) of, U.S. Utility application Ser. No. 16/565,104 titled "Nutraceutical Composition Comprising C60 And Ketone Esters" by the same inventor, filed on Sep. 9, 2019. This application also claims priority to, and is a continuation in part (CIP) of U.S. Utility application Ser. No. 16/589,715 titled "Nutraceutical Compositions Comprising C60 and Curcumin" by the same inventor, filed on Oct. 1, 2019. Both applications are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is nasal spray.

BACKGROUND

The following description includes information that may be useful in understanding the present invention. It is not an admission that any of the information provided herein is prior art or relevant to the presently claimed invention, or that any publication specifically or implicitly referenced is prior art.

Certain respiratory conditions are some of the most difficult diseases to treat. For example, asthma attacks are caused by swollen and inflame airways. Although symptoms of asthma can be managed by steroids, currently there is no cure for asthma. In another example, nasal polyps are associated with asthma, recurring infection, allergies, drug sensitivity or certain immune disorders. Treatment options for nasal polyps are limited as invasive surgery appears to be the only option which can cause irreversible damage to healthy tissues.

Thus, there is still a need for new treatment options for certain respiratory conditions.

DETAILED DESCRIPTION OF THE INVENTION

Figure 1:
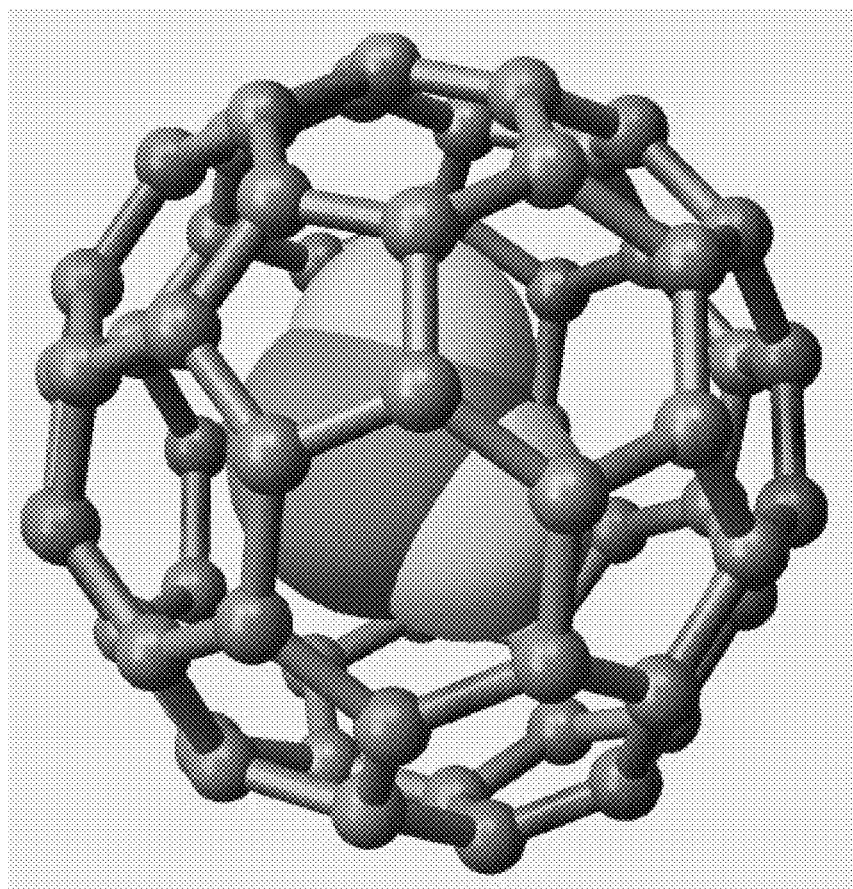
FIG. 1 is a diagram of a molecule (e.g., curcumin) inside C60 molecule.

The inventive subject matter provides compositions and methods in which fullerene (e.g., C60), curcumin, and black seed oil, are used to treat respiratory conditions through nasal spray, inhaling, or oral administration.

The contemplated nutraceutical compositions contain, as primary ingredients, a fullerene, curcumin, and a medium chain triglyceride. The medium chain triglyceride can be provided by using black seed oil, or other oils (olive, avocado, coconut, sunflower, etc.). Black seed oil is derived from the seeds of *Nigella sativa*, a small plant that grows in Eastern Europe, Western Asia, and the Middle East. In especially preferred embodiments, buckminsterfullerene C60 is used as the fullerene. Curcumin is the major polyphenol in the spice turmeric. Tetrahydrocurcumin (THC), which is a product of bacterial or intestinal metabolism of curcumin. Tetrahydrocurcumin has differing positive effects and color from curcumin. Either curcumin or tetrahydrocurcumin could be utilized depending on the health issue being treated. It is further contemplated that curcumin and tetrahydrocurcumin are used in combination.

In preferred embodiments, medium chain triglyceride (e.g., blackseed oil) is advantageously mixed with curcumin first, and then mixed with fullerene (e.g., C60). This sequential addition ensures that the curcumin and blackseed oil bond first and then are absorbed inside the C60 structure, resulting a homogeneous mixture of curcumin and blackseed oil inside C60. This allows curcumin and blackseed oil to cross the blood-brain barrier as carried by the C60 molecule, such that brain disorders can be effectively treated. It is contemplated that the composition and methods described herein can treat brain disorders, including Alzheimer's disease, dementia, brain cancer, epilepsy, mental disorders, Parkinson's disease, stroke, cerebral microbleeds, and transient ischemic attack.

It is contemplated other compounds can be put into a fullerene in similar manner, that is, by mixing with oil first, and then mix with fullerene. For example, in FIG. 1, a molecule (e.g., curcumin, or curcumin bonded with another molecule) is placed inside a C60 molecule. In some embodiments, the nutraceutical composition's active ingredients consist essentially of fullerene, curcumin, and black seed oil. In some embodiments, the nutraceutical composition further comprises beta-hydroxybutyrate (BHB).

The nutraceutical composition can be packaged in gel capsules for oral consumption, as a nasal spray in a mist-producing device, or as an inhaler that can produce steam or mist to be inhaled through the nose or the mouth. Accordingly, the nutraceutical composition can be administered by orally, by spraying into the nose, by inhaling through the mouth, or any combination thereof. Moreover, saline (i.e., saltwater) can be added to the nasal spray or inhaler to facilitate delivery. It is contemplated that nasal spray, inhaler, and gel capsules can be used individually or in combination, to treat respiratory conditions or brain disorders.

In some embodiments, the nutraceutical composition is a solution or a suspension of small particles having a size no greater than 0.5 In preferred embodiments, the nutraceutical composition is substantially free of particles having a size of greater than 0.2 It is contemplated that this can be achieved by filtering the composition with a filter having a pore size of 0.5 μm, or 0.2 μm. As used herein, "size" refers to the longest distance from one end of a particle to another end of the particle. As applied to a particle with a spherical shape, "size" refers to its diameter.

The inventive subject matter also provides methods for treating respiratory conditions. Contemplated respiratory conditions that can be treated or prevented with the composition and methods described herein include asthma, pneumonia, bronchitis, nasal congestion, turbinate hypertrophy, nasal polyp, lung cancer, influenza, chronic obstructive pulmonary disease (COPD) chronic bronchitis, emphysema, tuberculosis, and cystic fibrosis/bronchiectasis.

Anecdotal evidence from human volunteers has demonstrated that the nutraceutical composition according to teachings herein has unexpected benefits in treating severe asthma. After taking internally, a volunteer having severe asthma noticed significant reduction in asthma symptoms. After using the nutraceutical composition as an inhaler, the volunteer is completely free from asthma symptoms. In other volunteers, after using the nutraceutical composition as a nasal spray, nasal polyps unexpectedly fell out of nasal passage.

The inventive subject matter also teaches use of a composition to treat a respiratory condition, wherein the composition comprises a fullerene, curcumin, and a medium chain triglyceride. The use of composition to treat a respiratory condition, including asthma, pneumonia, bronchitis, nasal congestion, turbinate hypertrophy, nasal polyp, lung cancer, influenza, chronic obstructive pulmonary disease (COPD) chronic bronchitis, emphysema, tuberculosis, and cystic fibrosis/bronchiectasis. The medium chain triglyceride can be black seed oil, olive oil, avocado oil, coconut oil, sunflower oil, or any combination thereof. The fullerene preferably C60. The composition can further comprise saline.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A nasal spray, comprising C60, curcumin, and black seed oil, packaged in a mist-producing device, wherein black seed oil is mixed with curcumin first, then mixed with C60, and wherein the composition is substantially free of particles having a size of greater than 0.2 μm.

2. The nasal spray of claim 1, wherein the nasal spray further comprises saline.

3. The nasal spray of claim 1, wherein the nasal spray further comprises beta-hydroxybutyrate.

4. The nasal spray of claim 1, wherein at least some curcumin molecules are inside C60 molecules.

5. The nasal spray of claim 1, wherein the nasal spray further comprises tetrahydrocurcumin.

6. A method of treating a respiratory condition, comprising administering to a recipient, a nutraceutical composition comprising C60, curcumin, and black seed oil, wherein black seed oil is mixed with curcumin first, then mixed with C60, and wherein the nutraceutical composition is substantially free of particles having a size of greater than 0.2 μm.

7. The method of treating a respiratory condition in claim 6, wherein the respiratory condition is asthma.

8. The method of treating a respiratory condition in claim 6, wherein the nutraceutical composition is administered orally.

9. The method of treating a respiratory condition in claim 6, wherein the nutraceutical composition is administered by spraying into a nostril of the recipient.

10. The method of treating a respiratory condition in claim 6, wherein the nutraceutical composition is administered by inhaling.

11. The method of treating a respiratory condition in claim 6, wherein the medium chain triglyceride is mixed with curcumin first, then mixed with fullerene.

12. A use of a composition to treat a respiratory condition, wherein the composition comprises C60, curcumin, and black seed oil, wherein black seed oil is mixed with curcumin first, then mixed with C60.

13. The method of treating a respiratory condition in claim 6, wherein the respiratory condition is nasal polyp.

* * * * *